US00PP17236P3

(12) United States Plant Patent
Hanes

(10) Patent No.: US PP17,236 P3
(45) Date of Patent: Nov. 28, 2006

(54) ***PELARGONIUM* PLANT NAMED 'AMRI DERED'**

(50) Latin Name: *Pelargonium×hortorum*
Varietal Denomination: Amri Dered

(75) Inventor: Mitchell E. Hanes, Morgan Hill, CA (US)

(73) Assignee: Goldsmith Seeds, Inc., Gilroy, CA (US)

( * ) Notice: Subject to any disclaimer, the term of this patent is extended or adjusted under 35 U.S.C. 154(b) by 186 days.

(21) Appl. No.: 11/091,203

(22) Filed: Mar. 28, 2005

(65) Prior Publication Data

US 2006/0218686 P1 Sep. 28, 2006

(51) Int. Cl.
*A01H 5/00* (2006.01)

(52) U.S. Cl. ..... Plt./330
(58) Field of Classification Search ..... Plt./330
See application file for complete search history.

*Primary Examiner*—Kent Bell
(74) *Attorney, Agent, or Firm*—Jondle & Associates P.C.

(57) ABSTRACT

A *Pelargonium* cultivar particularly distinguished by its bright, rich red flower color and semi-double flowers is disclosed.

1 Drawing Sheet

Figure 1:
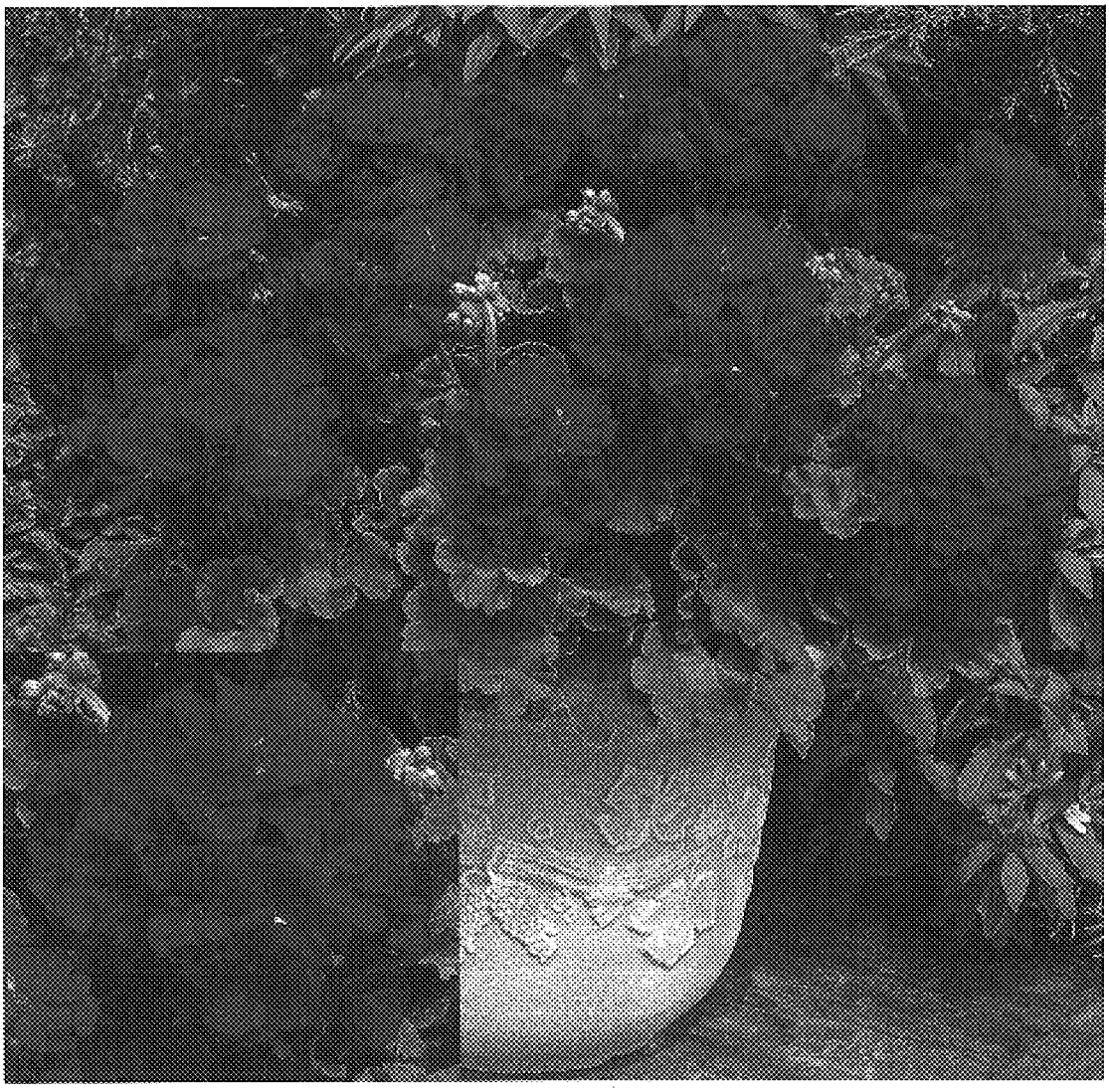

Genus and species: *Pelargonium×hortorum* L.H. Bailey. Variety denomination: 'Amri Dered'.

BACKGROUND OF THE NEW PLANT

The present invention comprises a new and distinct cultivar of *Pelargonium*, botanically known as *Pelargonium× hortorum* L.H. Bailey, and hereinafter referred to by the cultivar name 'Amri Dered'. The new cultivar was propagated from a seedling resulting from the cross of 8691-2, a dark red-flowered, unnamed, unpatented proprietary *Pelargonium* line, as the female parent, and 'Rumba Fire', a scarlet-flowered *Pelargonium* (U.S. Plant Pat. No. 12,489), as the male parent.

The new cultivar was created in 2000 in Gilroy, Calif. and has been asexually reproduced repeatedly by vegetative cuttings in Gilroy, Calif. over a four year period. It has also been trialed at Gilroy, Calif., Litchfield, Mich., and Andijk, The Netherlands. It has been found to retain its distinctive characteristics through successive asexual propagations. 'Amri Dered' reproduces true to type through successive generations of asexual reproduction.

DESCRIPTION OF PHOTOGRAPH

This new geranium plant is illustrated by the accompanying photograph which shows blooms, buds, and foliage of the plant; the colors shown are as true as can be reasonably obtained by conventional photographic procedures. The photograph is of a 4 month old plant grown in a lexan-covered greenhouse with other zonal *pelargonium* culture.

FIG. 1. shows overall plant habit while the inset photograph show a closer view of the mature inflorescence.

DESCRIPTION OF THE NEW CULTIVAR

The following detailed descriptions set forth the distinctive characteristics of 'Amri Dered'. The data which defines these characteristics were collected from asexual reproductions carried out in Gilroy, Calif. The plant history was taken on seven-month-old plants grown in 1 gallon pots in a poly-covered greenhouse during the fall/winter season. The color readings were taken under natural light in the greenhouse in the late winter season. Color references are primarily to The R.H.S. Colour Chart of The Royal Horticultural Society of London (R.H.S.) (2001). Texture description data were collected by viewing plant parts with a dissecting microscope.

DETAILED BOTANICAL DESCRIPTION

Classification:

*Botanical.*—*Pelargonium×hortorum* L.H. Bailey.

*Common name.*—Geranium.

Growth:

*Form.*—Upright, outwardly spreading and rounded growth habit.

*Growth and branching habit.*—Good vigorous habit, well branched.

*Height.*—15–23 cm as measured from soil level to top of plant, excluding blooms; 20–25 cm from soil level to top of umbels.

*Width.*—35–45 cm excluding umbels.

*Time to produce a finished flowering plant.*—8–10 weeks.

*Outdoor plant performance.*—Has good weather tolerance; used in hanging baskets, patio or mixed containers.

*Time to initiate and develop roots.*—12–28 days.

*Root description.*—White, slightly pubescent, fibrous yet coarse.

Leaves:

*Arrangement.*—Alternate, simple.

*Immature leaf.*—Color: Upper surface: RHS 146A. Lower surface: RHS 146B. Length: 4.5–4.7 cm. Width: 5.5–7.5 cm.

*Mature leaf.*—Color: Upper surface: Between RHS 146A and RHS 146B. Lower surface: RHS 146B. Length: 6.0–6.5 cm. Width: 10.0–10.5 cm.

*Zonation color.*—Faint shading of RHS N199B.

*Zonation diameter.*—1.5–2.0 cm.

*Apex description.*—Rounded.

*Base description*.—Cordate.
*Shape*.—Reniform.
*Margin*.—Crenate; somewhat sinuate.
*Texture*.—Pilose, velvety.
*Venation*.—Palmate.
*Venation color*.—RHS 144A.
*Petioles*.—Length: 9.0–10.0 cm. Diameter: 0.35 cm. Color: RHS 144A. Texture: Pilose; some glandular hairs.

Stems:
*Length*.—20–25 cm.
*Internode length*.—1.0–1.5 cm.
*Color*.—RHS 144B.
*Texture*.—Pilose; many glandular hairs.

Flower buds:
*Diameter*.—0.7–0.9 cm.
*Length*.—0.9–1.3 cm.
*Shape*.—Elliptical.
*Color when sepals first divide*.—RHS 45B.

Inflorescence:
*Type*.—An umbel composed of 13–16 flowers.
*Umbel diameter*.—8.0–9.0 cm.
*Umbel depth* (*height*).—5.6 cm.
*Blooming habit*.—Continuous blooming throughout the growing season; good floriferousness.
*Peduncle*.—Length: 14–15 cm. Diameter: 0.5 cm. Texture: Pilose; many glandular hairs. Color: RHS 144A.
*Pedicel*.—Length: 1.7–1.8 cm. Diameter: 0.1 cm. Texture: Many glandular hairs. Color: RHS 144A.

Flowers:
*Flower form*.—Polypetalous; mostly imbricate petals and petaloids, semi-double form consisting of 7–9 petals and 1–3 petaloids.
*Flower diameter*.—4.5–5.3 cm.
*Flower persistence*.—An open flower will hold its petals until the flower begins to dehisce, 7–10 days.
*Fragrance*.—None.

Petals/petaloids:
*Petal size*.—Length: 2.5–2.9 cm. Width: 2.3–2.7 cm.
*Shape*.—Obovate.
*Apex*.—Rounded.
*Base*.—Acute.
*Margin*.—Entire.
*Texture*.—Papillose.
*Upper petal color*.—Upper surface: Velvety RHS 44B but brighter and richer, with basal veining a faint RHS 46B. Lower surface: RHS 44B with streaks of RHS 44A basally.
*Lower petal color*.—Upper surface: Velvety RHS 44B but brighter and richer, with basal veining a faint RHS 46B. Lower surface: RHS 44B.
*Upper petaloid color*.—Upper surface: Velvety RHS 44B but brighter and richer, with basal veining a faint RHS 46B.
*Lower petaloid color*.—Upper surface: Velvety RHS 44B but brighter and richer, with basal veining a faint RHS 46B.
*Color change with age*.—Colors do not change with age but may change with temperature and time of year.

Sepals:
*Number of sepals*.—5, one larger than the others; fused at base.
*Length of sepals*.—0.9–1.0 cm.
*Width of sepals*.—0.2–0.4 cm.
*Shape*.—Oblanceolate.
*Apex*.—Acuminate.
*Texture*.—Pilose, villous; many glandular hairs.
*Color*.—RHS 144A.

Reproductive organs:
*Stamens*.—4–6, sometimes fused to petaloids.
*Filament color*.—RHS N155B but whiter.
*Filament length*.—0.6 cm.
*Pollen color*.—RHS N30A.
*Pollen amount*.—Scant to moderate.
*Pistil*.—1.
*Pistil length*.—0.9 cm.
*Stigma color*.—RHS 42A.
*Style color*.—RHS 39A.
*Style length*.—0.8 cm.
*Fruit set*.—Not observed.

Disease and insect resistance: Not observed.

Comparison with Known Cultivars

When the instant plant is compared to the female parental cultivar 8691-2, 'Amri Dered' has double flowers, faint zone on the leaf, and upright habit with better branching than 8691-2. When 'Amri Dered' is compared to the male parental cultivar 'Rumba Fire' (U.S. Plant Pat. No. 12,489), 'Amri Dered' has dark red flowers, is more free flowering and has a lighter and narrower zone on the leaves than 'Rumba Fire'.

'Amri Dered' differs from the comparison variety, 'FIP 553' (U.S. Plant Pat. No. 13,961) also known as 'Rocky Mountain Red 2003' by having larger leaves, a shade darker flower and more petals than 'Rocky Mountain Red 2003'.

I claim:

1. A new and distinct cultivar of *Pelargonium* plant as shown and described herein.

* * * * *